US012318140B2

(12) United States Patent
Zimmerman

(10) Patent No.: US 12,318,140 B2
(45) Date of Patent: Jun. 3, 2025

(54) SYSTEM AND METHOD FOR DETERMINING PRESCRIPTION OF CORRECTIVE LENSES USING PREDICTIVE CALCULATIONS AND CORRECTED-EYESIGHT SIMULATION

(71) Applicant: Digiteyez Corporation, Wilmington, DE (US)

(72) Inventor: Brandon Zimmerman, Washington, DC (US)

(73) Assignee: Digiteyez Corporation, Wilmington, DE (US)

( * ) Notice: Subject to any disclaimer, the term of this patent is extended or adjusted under 35 U.S.C. 154(b) by 1148 days.

(21) Appl. No.: 17/097,545

(22) Filed: Nov. 13, 2020

(65) Prior Publication Data

US 2021/0145271 A1     May 20, 2021

Related U.S. Application Data

(60) Provisional application No. 62/935,407, filed on Nov. 14, 2019.

(51) Int. Cl.
*A61B 3/00* (2006.01)
*A61B 3/032* (2006.01)
(Continued)

(52) U.S. Cl.
CPC ............ *A61B 3/0025* (2013.01); *A61B 3/032* (2013.01); *A61B 3/103* (2013.01); *A61B 3/1035* (2013.01);
(Continued)

(58) Field of Classification Search
CPC ....... A61B 3/0025; A61B 3/032; A61B 3/103; A61B 3/1035; A61B 3/132; A61B 3/0285;
(Continued)

(56) References Cited

U.S. PATENT DOCUMENTS 7,354,156 B1 *  4/2008  McLeod ................ A61B 3/032
                                                              351/203
9,241,620 B1 *  1/2016  Kockan ................. G06F 3/0482
(Continued)

FOREIGN PATENT DOCUMENTS

WO    2005/050290    6/2005
WO    2017/134275    8/2017
(Continued)

OTHER PUBLICATIONS

Tan. Doctoral Dissertation: Optical Modeling of Schematic Eyes and the Ophthalmic Applications. 118-175, 2009 [retrieved on Feb. 3, 2021]. Retrieved from the Internet. <URL: https://trace.tennessee.edu/cgi/viewcontent.cgi?referer=https://www .google.com/&httpsredir= 1&article=1093&context=utk_graddiss> entire document.
(Continued)

*Primary Examiner* — Mohammed A Hasan
(74) *Attorney, Agent, or Firm* — HOGAN LOVELLS US LLP

(57) ABSTRACT

This is a system and method for determining a patient's prescription for corrective lenses using predictive calculations and corrected-eyesight simulation. Together, these technologies act as a digital substitute for phoropter testing, thus reducing the cost, time, and human error associated with an eye exam. Based on age, gender, autorefractor readings, and environmental factors, a patient specific model is calculated and fed into a visual simulation tool. From this simulation, an eye care professional is able to determine the patient's corrective lens prescription.

8 Claims, 10 Drawing Sheets

(51) Int. Cl.
  *A61B 3/103* (2006.01)
  *A61B 3/13* (2006.01)
  *G02C 7/02* (2006.01)
  *G06F 30/20* (2020.01)
(52) U.S. Cl.
  CPC .............. *A61B 3/132* (2013.01); *G02C 7/024* (2013.01); *G06F 30/20* (2020.01)
(58) Field of Classification Search
  CPC ......... G02C 7/024; G02C 7/027; G06F 30/20; G16H 50/50
  USPC .......................................................... 351/200
  See application file for complete search history.

(56) References Cited

U.S. PATENT DOCUMENTS

| | | | |
|---|---|---|---|
| 11,464,406 B2 * | 10/2022 | Lai | A61B 3/0008 |
| 2013/0261782 A1 | 10/2013 | Becken et al. | |
| 2014/0211166 A1 * | 7/2014 | Scherlen | A61B 3/02 |
| | | | 351/239 |
| 2016/0120402 A1 * | 5/2016 | Limon | A61B 3/0033 |
| | | | 351/239 |
| 2016/0302660 A1 | 10/2016 | Bühren | |
| 2017/0177166 A1 | 6/2017 | Kockan | |
| 2018/0192869 A1 * | 7/2018 | Lee | A61B 3/0025 |
| 2019/0012784 A1 | 1/2019 | Wiley | |
| 2019/0110890 A1 | 4/2019 | Rosen et al. | |

FOREIGN PATENT DOCUMENTS

| | | |
|---|---|---|
| WO | 2019/165262 | 8/2019 |
| WO | 2019178862 A1 | 9/2019 |

OTHER PUBLICATIONS

International Search Report and Written Opinion mailed Mar. 25, 2021 in PCT/US2020/060418.
Extended European Search Report issued in related EP Application No. 20887626.8, dated Feb. 9, 2024.

* cited by examiner

Steps in Method for Determining a Prescription for Corrective Lenses

SYSTEM AND METHOD FOR DETERMINING PRESCRIPTION OF CORRECTIVE LENSES USING PREDICTIVE CALCULATIONS AND CORRECTED-EYESIGHT SIMULATION

CROSS REFERENCE TO RELATED APPLICATIONS

The present application claims priority to U.S. provisional patent application No. 62/935,407, filed on Nov. 14, 2019. The disclosure of the above-referenced application is hereby incorporated by reference.

FIELD OF THE INVENTION

The present invention is directed to a system and method for determining prescriptions of corrective lenses using predictive calculations and corrected-eyesight simulation, and more specifically to using specific patient inputs including age, gender, and autorefractor or tele-refraction readings in a simulation to determine a prescription.

BACKGROUND OF THE INVENTION

Most vision problems are caused by refractive errors. During a typical eye examination, an eye care professional will diagnose refractive errors and prescribe corrective lenses. There are two components to a typical eye examination: (1) objective refraction and (2) subjective refraction. Objective refraction occurs at the beginning of an eye exam when an automated refractor (the "autorefractor") is used to measure the patient's eyes. The autorefractor is a computer-controlled machine that provides an objective measurement of a patient's refractive error. Typically, the autorefractor displays an image that shifts in and out of focus until it can attempt to measure the patient's refractive error, and then outputs an estimated prescription which eye care professionals use to determine the final prescription. This estimated prescription is often imprecise due to the way the eye responds to the autorefractor—including accommodation, depth of focus, and spherical aberrations.

Subjective refraction is the second phase of an eye exam. It helps eye care professionals to better define the patient's needed prescription by using a phoropter—an instrument with several rotating lenses that the patient looks through while reading a Snellen chart. As the eye care professionals begin with the starting point provided by the autorefractor, they then cycle through various combinations of lenses in the phoropter, asking the patient to convey which lens combination provides a "better or worse" image. This process eliminates any imprecision in the prescription estimated by the autorefractor. This process is repeated until the patient subjectively determines the prescription that allows them to achieve 20/20 vision (or, as close as possible to) when reading the Snellen chart. This second phase of the eye exam relies on subjective judgement and communication between the patient and eye care professional. Inexperienced patients, miscommunication, and errors in judgment can result in a flawed prescription.

Equipment such as phoropters have been largely unchanged since the beginning of the 20$^{th}$ century. They are expensive, spatially inefficient, and are time-consuming to use. As a result, billions of people across the world do not have access to quality eyecare.

A system and method is needed that overcomes the imprecision of autorefractor readings and eliminates the potential human error associated with phoropters, in addition to improving the availability and cost of eye care.

SUMMARY

The present invention is directed to a system and method for determining a patient's eyeglass prescription using predictive calculations and corrected-eyesight simulation. The system and method provide a digital substitute for phoropter testing, reducing the cost, time, equipment space, and potential human error associated with an eye exam. The present invention therefore allows more people to have access to quality eyecare. This increased access will improve the health of patients, in addition to saving them time, frustration, and money. The present invention will also allow eye care professionals to see more patients and improve service quality, which will increase their patient roster and generated revenue.

Most research studies of the eye tend to only investigate one natural parameter (age variation, gender variation, pupil variation, etc.) at a time. The systems and methods described herein unify multiple parameters into a single model for first order refractive error correction. Most existing application models of the eye do not take into account the toric shape of the cornea, nor the inhomogeneous index structure of the crystalline lens, and instead follow the fixed Gullstrand values for thickness, and curvatures. Furthermore, these existing models do not account for the spherical aberration of the cornea, which is an important visual aberration that eyeglass cannot correct for, and thus must be accounted for. Nor do the existing models account for accommodation in a functional form. The model of the system and method described herein accounts for and unifies all of these parameters, and others, (to first order), in order to represent the patient's eye in its most natural form at the time of an eye exam.

The present invention discloses a predictive calculation method that uses data about the patient and environment to generate a representation of the patient's vision that accounts for a plurality of parameters of visual acuity simultaneously. This patient-specific model is used to run an optical ray trace, refractive error assessment, and neural correction. Based on the results, the method then produces a set of refractive Zernike coefficients and a suggested prescription, which are both fed into a vision simulation tool. This tool simulates patient performance on a virtual Snellen (or any vision) chart test, creating a digital corollary to the physical vision test performed in a traditional eye exam. From this simulation, an eye care professional is able to determine whether a patient can qualitatively and quantitatively achieve 20/20 visual performance. If necessary, the simulated prescription can be iterated, in the same manner a traditional phoropter allows, to reach 20/20 vision.

DETAILED DESCRIPTION

The present invention is directed to a system and method for determining a patient's eyeglass prescription using predictive calculations and corrected-eyesight simulation. By relying on readings generated by a traditional autorefractor (e.g., 701 in FIG. 7), the system and method generates a digital model of the patient eye and calculates a prescription without any additional patient input.

Figure 1:
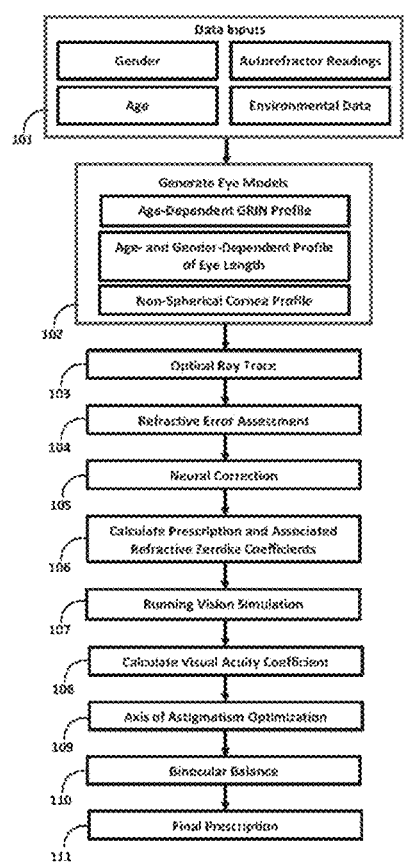
FIG. 1 is a flow chart showing steps in a method for determining a prescription for corrective lenses.

FIG. 1 describes a method for determining a prescription of corrective lenses, which may include the following steps. First, in step 101, certain patient-specific and environmental data are input into the data storage system. The patient-specific data may include age, gender, autorefractor readings, or other data. The patient-specific data may be obtained directly from the patient, or may be received from other medical professionals. The autorefractor readings may be taken by the eye care professional, or may be provided to the eye care professional. Generally, autorefractor readings estimate the refractive power of the cornea, though the specific readings may vary between autorefractor machines. Other environmental data such as room geometry and lighting may be gathered, because these factors may affect pupil size and eye relaxation.

Next, in step 102, the patient-specific and environmental data are used to generate a model of the patient eye. This model may include any of the following patient profiles: (1) an age-dependent Gradient Index profile (the "GRIN profile") of the internal optics of the eye, (2) an age- and gender-dependent profile of the length of the eye, and (3) a non-spherical (toric) cornea profile that defines the patient's sphero-cylindrical refractive power. In at least one embodiment, the process begins with the standard GRIN profile varying material (such as the crystalline lens found in the human eye), and then the process (a) re-scales its thickness with respect to the age of the patient and (b) normalizes its new thickness to the appropriate optical thickness ratios found in the inhomogeneous layers that make up the crystalline lens. Patient age is used to scale the various internal age-dependent components of the human eye. Patient gender is used to scale the internal gender-dependent components of the human eye. Autorefractor readings are converted into cornea parameters that are used to model the primary toric (sphero-cylindrical) surface of the eye that account for the refractive error (e.g., near sightedness, far sightedness, and astigmatism) as well as spherical aberration. These refractive readings are then converted to refractive Zernike coefficients. The final output of step 102 is an optical model of the patient's accommodated naked eye with no prescription correction, and the refractive Zernike coefficients associated with that model.

While most existing optical models study one parameter of visual performance at a time, or follow the Gullstrand homogeneous eye model, the multi-profile model resulting from step 102 accounts for several parameters of a vision prescription simultaneously (including accommodation). This allows it to digitally model and assess the visual acuity of the eye in real time. The model of the patient's eye serves as the baseline of an individual patient's visual system, and forms the basis for the steps in the method for determining a prescription of corrective lenses described herein.

Once the eye model is generated, in step 103, an optical ray trace is performed on the profile to simulate how light from an autorefractor reaches the retina, and how the eye responds to the autorefractor environment (e.g., accommodation, pupil size, depth of focus). This ray trace may be performed with standard ABCD optical ray tracing, such that a representation of the optical system (eye) can be expressed with a series of matrices. These matrices consist of the physical parameters of each surface that make up the eye. A set of computer generated optical rays are then propagated through the optical system with matrix multiplication, until the final rays are calculated at the image plane (retina). This trace allows for an additional analysis of the refractive error and overcomes the imprecision of traditional autorefractor readings. The trace is performed on both the spherical and cylindrical axis.

Next, in step 104, the refractive error assessment allows for quantification of the various components of the refractive error for each patient in terms of defocus (near sighted and far sightedness), spherical aberration, depth of focus, and accommodation. Standard autorefractors often lump these errors into a single prescription value, resulting in prescriptions that are erroneously under- or overcorrected. While these under- or overcorrection errors have traditionally been manually eliminated using a phoropter, the method described herein digitally removes such errors in a matter of seconds. This removal is done by defining physical and optical boundaries with respect to the physical dimensions of that patient's eye, and principles of geometrical optics in the visual system. Light from the optical ray trace is measured with respect to these boundaries. The algorithm then assesses any deviations from the retina as error. Any error is then quantified in terms of its source (e.g., aberrations, accommodation) and converted into diopters.

Step 105 is the neural correction process. Due to optical uncertainties within the autorefractor, the source of error can be quantified as an overcorrection or undercorrection. Similar to how the brain communicates with the eye to achieve the best image possible for the patient, this neural correction process simulates these conditions based off various visual optics scenarios—for example, accommodation, depth of focus, and center of least confusion—to ultimately assess whether the autorefractor prescription is under- or overcorrecting and adjusts accordingly.

Figure 2:
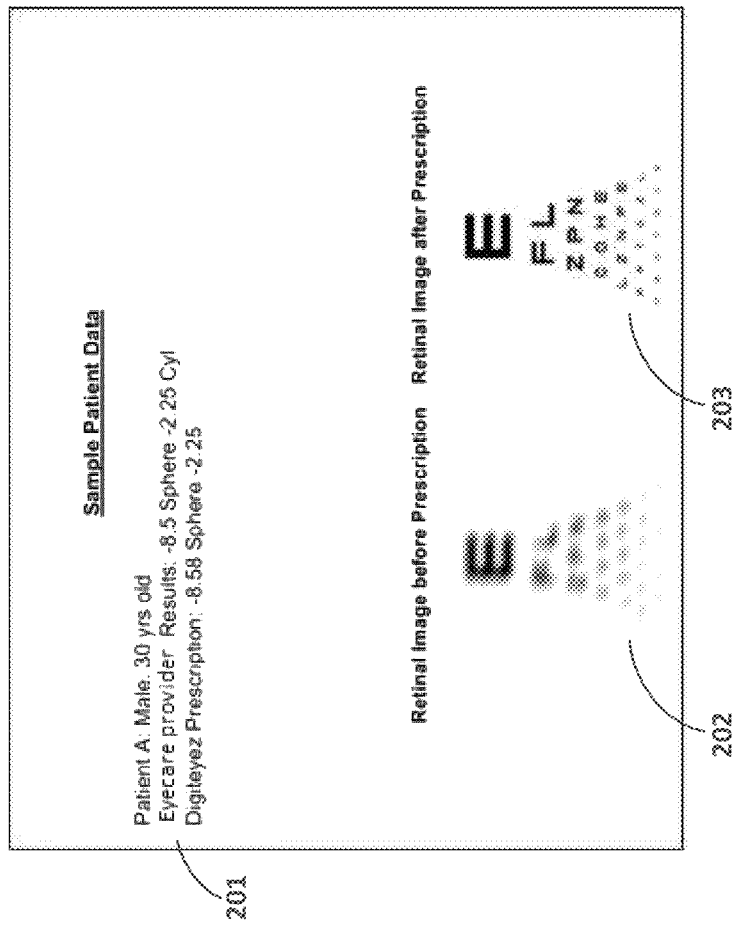
FIG. 2 provides example comparisons of simulated patient eyesight before and after corrective prescription, as determined by predictive calculations.

Once all errors are accounted for, in step 106, another ray trace is performed on the patient eye model to calculate a suggested prescription for the patient. In this step, a new set of refractive Zernike coefficients are calculated that represent the corrected vision of the patient. These coefficients are saved, along with the coefficients calculated for the naked uncorrected eye in step 102, to be used in the remaining steps. FIG. 2 shows an example of a patient's suggested prescription calculated in step 106 as compared to the patient's prescription calculated by an eye care provider in a traditional eye exam. The retinal image after prescription 203, which is based on the patient's suggested prescription 201, is appreciably better than the retinal image before prescription 202.

Figure 8:
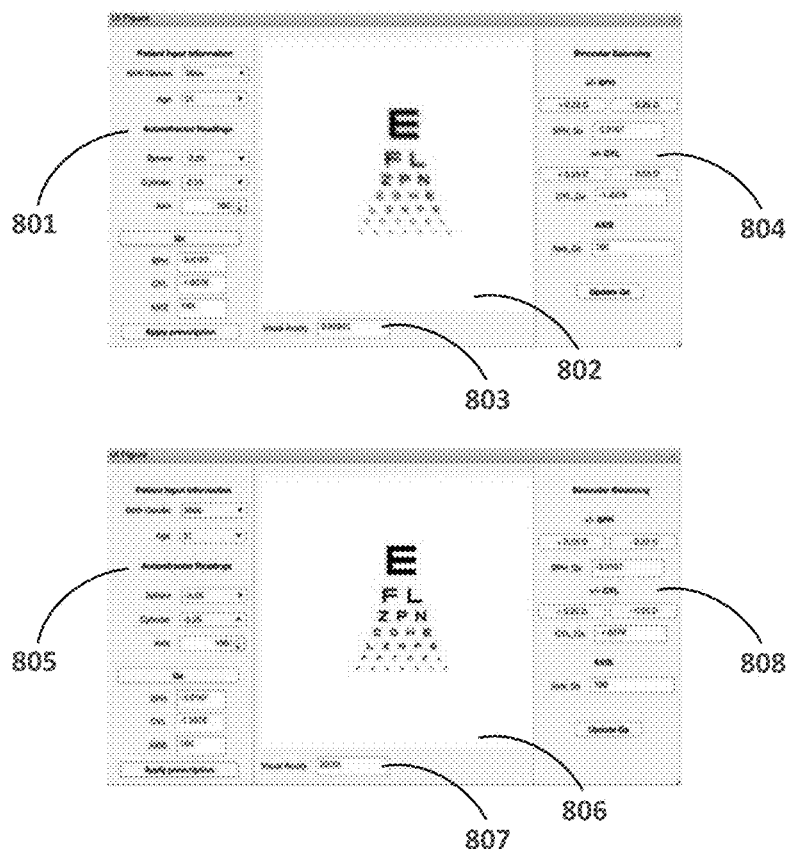
FIG. 8 is an image of the user interface being run on a computer as opposed to the phoropter.

Next, in step 107, the refractive Zernike coefficients calculated in steps 102 and 106 are automatically input into a vision simulation tool. The vision simulation tool is implemented as a module in a program executed by a computer processor. A user interface allows an eye care professional to interact with the vision simulation tool. Once the vision simulation tool is loaded with the refractive Zernike coefficients and the prescription, the eye care professional has the ability to interact with the tool through the user interface, as shown in FIG. 8 and described below.

In step 108, the visual acuity coefficient is calculated. Using a correlation method that will be discussed below with a sampling of patients, the visual acuity coefficient can be used to digitally replicate the phoropter with quantitative results. The visual acuity coefficient is calculated using image simulation techniques that replicate a patient's view of the Snellen chart (e.g., FIG. 8), or any other vision chart.

Once the astigmatism refractive power correction has been calculated, in step 109, the axis of astigmatism is determined. This axis exists at the angle where the astigmatism correction power is applied. The autorefractor provides an estimated axis, but it is imprecise in the same way that the other readings are. Instead of relying on an imprecise autorefractor output, step 109 runs an optimization routine using the visual acuity coefficient and the enhanced contrast font. This process may use the autorefractor axis as a starting point, and then may iteratively optimize around this value until 20/20 vision is achieved using the value of the visual acuity coefficient. The contrast sensitivity associated with the enhanced font allows this very minute adjustment to be precisely calculated. This optimization routine may serve as a digital substitute for the Jackson Crossed Cylinder.

Finally, in step 110, the visual acuity coefficient may be used to quantitatively binocular balance the eyeglass prescription. Sometimes, a new prescription may create (a) too large of a change from the previous prescription or (b) a drastic difference between the left and right eye prescription. These differences can be too much for the eyes to adjust to. This is corrected by using a standard routine called binocular balance. While eye care professionals traditionally correct for this error using a phoropter or other manual lenses, this step isolates the dominant prescription as the input and utilizes the visual acuity coefficient as a metric for quantifying the binocular balance process. If the prescription change is deemed too large by the eye care professional, they may decrease the prescription in increments (e.g., 0.25 D). In doing so, the vision simulation tool will update the image simulation and re-calculate the visual acuity coefficient to ensure the patient still maintains 20/20 vision with each adjustment. If either eye has a prescription significantly larger than the other, then the two image simulation results are displayed side by side. The eye care professional may decrease the input prescription value of the dominant eye in increments (e.g., 0.25 D). This may be decreased until the visual acuity coefficients of both eyes are no longer equal. This process can also be automated.

After all of the above steps are completed, in step 111, the final corrective-lens prescription may be provided to the patient.

Various versions of image simulation have been performed in optical image processing. The previous steps in this method shown in FIG. 1 and described above include visual inputs from refraction measurements and $1^{st}$ order matrix ray tracing. In contrast, standard routines would require a wavefront aberrometer (e.g., Shack-Hartmann wavefront sensor), optical interferometry, and or $3^{rd}$ order wavefront analysis found in advanced optical ray trace software (e.g., Zemax or Code V). Inputs from devices such as these are not ideal in eye exam settings primarily due to education. Optometrists are trained in first order optics but not in physical optics, from which principles of wavefront aberrometers are derived. In fact, ophthalmologists have very little education in optics at all. Additionally, traditional wavefront aberrometers tend to operate at only one wavelength of light and with one eye at a time, whereas autorefractors do not. Even if a wavefront aberrometer does overcome these limitations, they tend to be relatively expensive and spatially inefficient when compared to the autorefractor solution.

Figure 3:
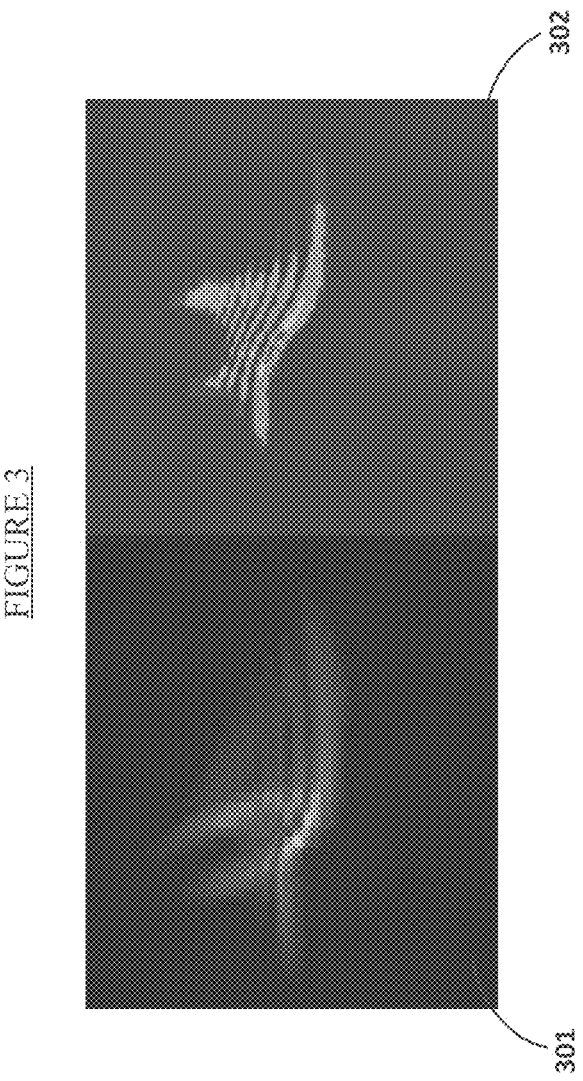
FIG. 3 is a point spread function (PSF) generated using a perfect lens with hard-coded refractive Zernike coefficients in CODE V (left) and the refractive PSF generated with same refractive Zernike coefficients in the vision simulation tool (right).

The method shown in FIG. 1 and described above effectively translates first order optics measurements into wavefront analysis, while still working in a language understood by optometrists and ophthalmologists. This achieves optimal results without the introduction of new and expensive examination hardware, and is capable of producing results with respectable accuracy when compared to commercialized optical ray tracing software that rely on the aforementioned concepts. This is demonstrated in FIG. 3, which compares the results of two attempts to generate a refractive point spread function ("PSF") for the same patient. PSFs are typically determined by advance ray tracing software or wavefront sensing instruments. The PSF is important because the PSF contains all the necessary information needed to confirm the quality of the optical system (e.g., an eye). A perfect PSF represents a "perfect system." An aberrated PSF will be deformed with respect to the individual aberrations (e.g., near sighted, far sighted, astigmatism) such that the rays of light are influenced by when they propagate through the patient's eye. Being able to extract the visual aberration information from the PSF is what also allows correction with an eyeglass prescription. This concept is how the design of quality imaging systems including cameras and telescopes are determined. Image 301 shows a PSF generated using Code V, a commercialized optical and ray tracing software used by optical engineers to design, model, and simulate some of the most sophisticated and complex optical systems in optical engineering today with extreme precision and accuracy. Image 302 shows a PSF generated using the vision simulation tool described in step 107. Code V implements advanced ray tracing, using thousands of optical rays, and optical wavefront analysis to the third order and higher, while the vision simulation tool only uses first order optical analysis and geometrical ray tracing and refraction. Despite these differences, the Code V point spread function 301 has a nearly identical form to the vision simulation tool's point spread function 302.

Figure 4:
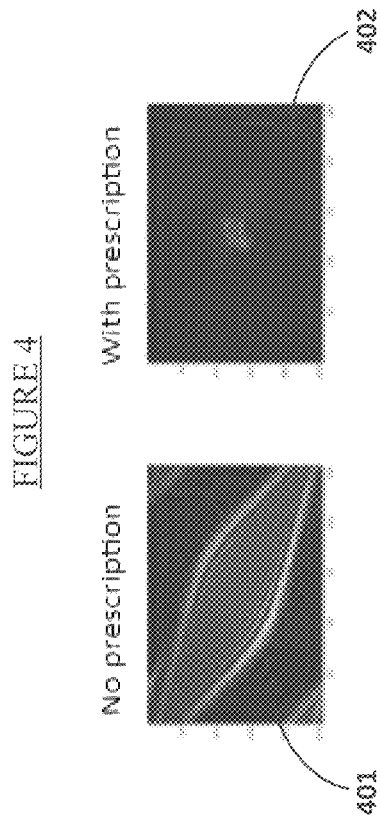
FIG. 4 is an example of the personalized refractive PSFs (uncorrected and corrected) the software generates for each patient to determine their individual prescriptions.

These Zernikes are then used to create a refractive optical PSF. As mentioned, PSFs are typically determined by advance ray tracing software or wavefront sensing instruments. Here, though, the PSF is determined through refraction. Examples of a patient's "before prescription" PSF and "after prescription" PSF are shown in FIG. 4. Larger distorted PSFs, like the one in image 401, are associated with non-corrected vision, whereas small compact PSFs, like the one in image 402, indicate corrected vision. FIG. 4 illustrates the system and method's ability to calculate and model both. By definition, the PSF is the response that the eye has to the point of the object it is viewing—here, the object is a Snellen chart. By performing a known mathematical technique called "the convolution" between the PSF and the Snellen image, this process simulates the patient's visual response to that input image. Thus, the output is a simulated image of how the patient views this reference Snellen chart to first order vision and correction. The output, after the autocorrelation between the reference and simulation images, reveals the percentage of how well correlated the images are to one another. At perfect correlation, this value is the highest. Using this correlation tactic, a sampling of patient visual acuity tests revealed a single autocorrelation value that is constantly achieved when patients have a prescription allowing them to see 20/20 vision. This value is referred to herein as the "visual acuity coefficient." The visual acuity coefficient enables the optimizations that occur in steps 109 and 110. For display purposes, the visual acuity coefficient will be accompanied with the respective image simulations of the Snellen reading chart used in all routine eye exams. This simulation provides a familiar visual and does not require an understanding of visual acuity coefficients. The eye care professional may show the patient the image simulation results to demonstrate the effectiveness of the prescription.

Figure 5:
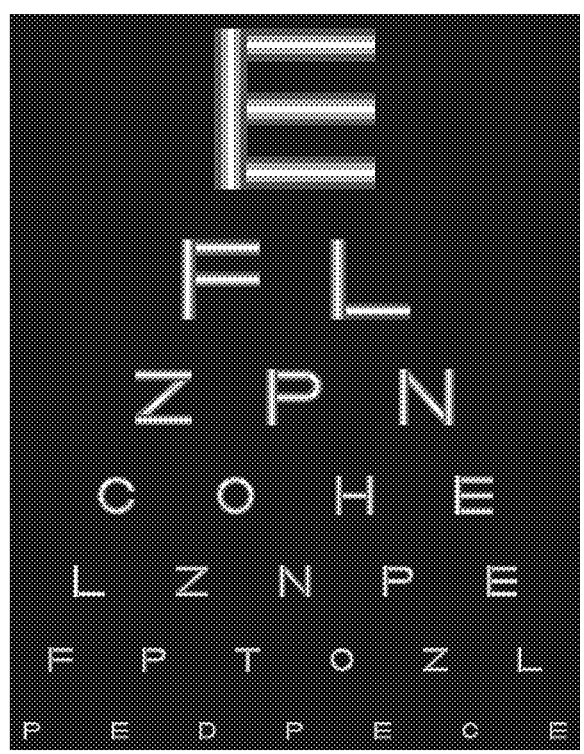
FIG. 5 is contrast visual acuity chart comprised of variable contrast font that the software uses for qualitative and quantitative image simulation analysis.

While the final image simulation results may be displayed with a standard Snellen chart with standard text (black font on white background), for improved digital accuracy the vision simulation tool may internally operate with an enhanced contrast font as portrayed in FIG. 5. Through the contrast sensitivity function, this enhanced font provides for better visual resolution in the presence of various forms of visual aberrations, including near sightedness, far sightedness and astigmatism. The letters are designed to maximize resolution in the presence of a small amount of defocus. Moderate spreading of the light from defocus only serves to fill in previously under-illuminated regions of the text away from the central bright bar of the limb. This enables integrity of the limbs of the text so that they can be resolved despite small amounts of defocus. The contrast is further shown in FIG. 6, where a letter E from the contrast-enhanced font (604) and a letter E from the typical Snellen font (602) are displayed in the presence of visual aberrations (603 and 601).

Figure 6:
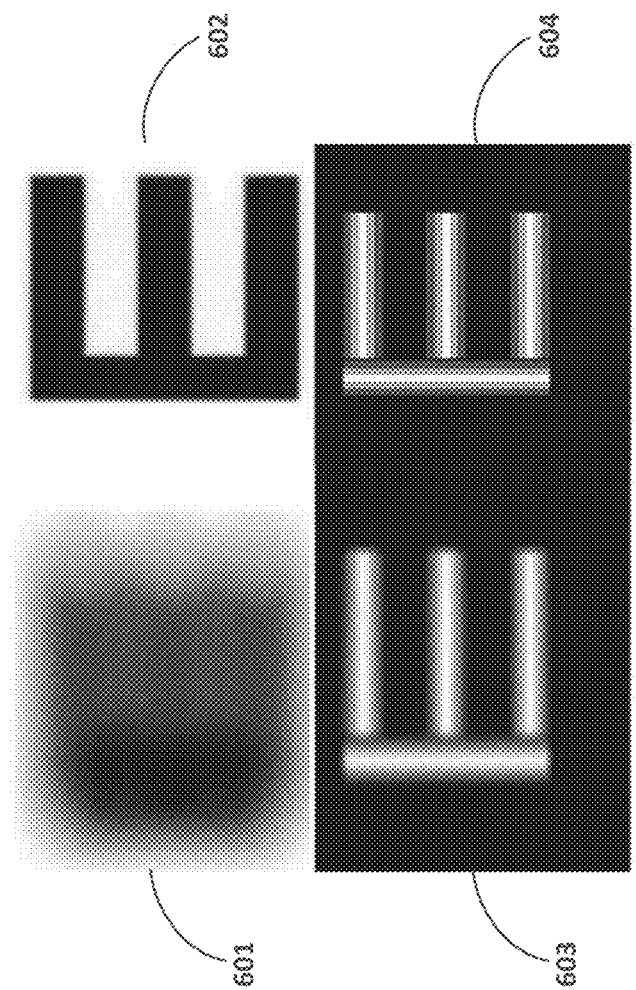
FIG. 6 provides a comparison example of how sensitive the standard font (top) compared to the contrasted font (bottom) is to uncorrected (left) and corrected (right) visual defocus.

The optical principles upon which the design depends are those of the point spread function and the line spread function and the edge spread function. As also seen in FIG. 6, a patient with corrected vision can resolve the individual contrast limbs within the letter in image 604. In the presence of defocus, as shown in image 603, the limbs become blurred into a solid letter, and the patient cannot resolve the individual limbs, but can still maintain resolvability of the full letter. This gives the eye care professional a more qualitative method of assessing the patients visual performance (counting limbs). Furthermore, FIG. 5 and images 603 and 604 are also more indicative of how patients see in the real world. The real world is not high contrast (e.g., black font on white background), but low contrast. Thus, a grayscale model of the Snellen chart using the contrast-enhanced font provides more accurate results when calculating the visual acuity coefficient because more real world information exists in this letter structure as opposed to standard black-and-white font.

Figure 7:
FIG. 7 provides an example of an eye care provider examining a patient with an autorefractor (left) and then a phoropter for subjective refraction (right).

FIG. 7 shows a prior art example of an example of an eye care provider examining a patient with an autorefractor (701) and a phoropter for subjective refraction (702).

FIG. 8 shows the user interface that allows an eye care professional to interact with the vision simulation tool, as described above with regard to step 107 of FIG. 1. Using this use interface, the eye care professional can view, input, or change the patient information (801 and 805). The user can also view the patient's visual performance in before images (802) and after images (806), view the algorithms calculation of the patient's ability to see 20/20 vision (803 and 807), modify the prescription in increments (e.g., +/−0.25 D) in order to perform common phoropter routines such as binocular balancing (804 and 808), and modify or optimize the axis of astigmatism if necessary (804 and 808). The vision simulation tool is an image processing technique for simulating a patient's visual acuity during the subjective component of a routine eye exam.

One metric for quantifying how well before-and-after images are "correlated" to each other is running a known image processing routine called the autocorrelation between the input reference Snellen chart, and the before and after Snellen images (802 and 806). The "before prescription" image (802) is how the reference Snellen chart is seen by a patient without the corrective prescription. The "after prescription" image (806) is how the reference Snellen chart is seen with the corrective prescription. The before and after images are generated using the input refractive Zernike coefficients calculated steps 102 and 106.

Figure 9:
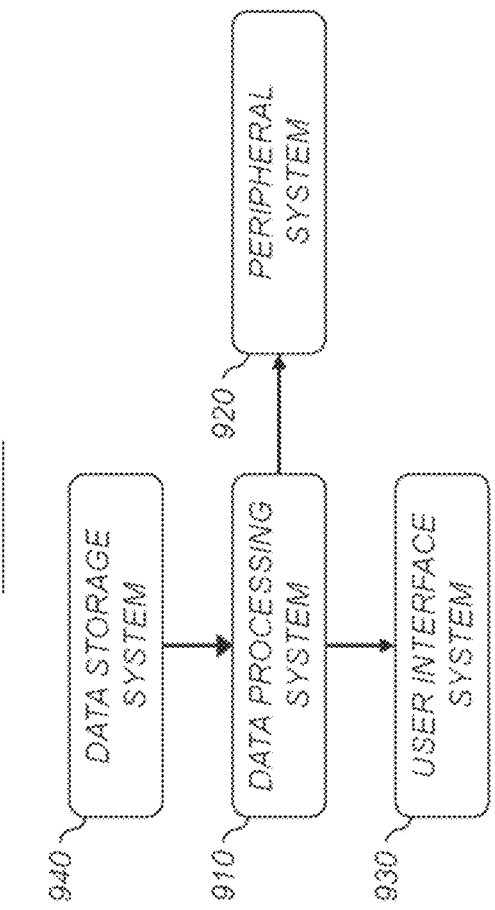
FIG. 9 is a high-level diagram showing the components of a computer system for generating a digital eye model and calculating a patient's prescription.

FIG. 9 is a high-level diagram showing the components of a computer system for generating a digital eye model and calculating a patient's prescription. The system includes a data processing system 910, a peripheral system 920, a user interface system 930, and a data storage system 940. The peripheral system 920, the user interface system 930 and the data storage system 940 are communicatively connected to the data processing system 910. These systems may be included within a desktop computer, or within a mobile device, such as a smartphone, tablet, or PDA. Alternatively, the patient data may be transmitted to a separate system for processing. For example, the desktop computer may transmit data to a server on a cloud computing network. The server may process the data, and transmit back a visual simulation and suggested prescription.

The data processing system 910 includes one or more data processing devices that implement the processes of the various embodiments of the present invention, including the example processes described herein. The data processing devices may be, for example, a central processing unit ("CPU"), a desktop computer, a laptop computer, a mainframe computer, a personal digital assistant, a smartphone, a tablet, a digital camera, cellular phone, or any other device for processing data, managing data, or handling data.

The data storage system 940 includes one or more processor-accessible memories configured to store information, including software instructions executed by the processor and captured image data. The data storage system 940 may be a distributed processor-accessible memory system including multiple processor-accessible memories communicatively connected to the data processing system 910 via a plurality of computers or devices. On the other hand, the data storage system 940 need not be a distributed processor-accessible memory system and, consequently, may include one or more processor-accessible memories located within a single data processor or device. The processor-accessible memory may be any processor-accessible data storage device, whether volatile or nonvolatile, electronic, magnetic, optical, or otherwise, including but not limited to, registers, floppy disks, hard disks, Compact Discs, DVDs, flash memories, ROMs, and RAMs.

The system components may be communicatively connected in any manner that enables transmissions of data between components, including wired or wireless transmissions between devices, data processors, or programs in which data may be communicated. This connection may include a connection between devices or programs within a single data processor, a connection between devices or programs located in different data processors, and a connection between devices not located in data processors at all. In this regard, although the data storage system 940 is shown separately from the data processing system 910, the data storage system 940 may be stored completely or partially within the data processing system 910. Further in this regard, although the peripheral system 920 and the user interface system 930 are shown separately from the data processing system 910, one or both of such systems may be stored completely or partially within the data processing system 910.

The peripheral system 920 may include one or more devices configured to provide patient data records to the data processing system 910. For example, the peripheral system 920 may include autorefractors, cellular phones, or other data processors. The data processing system 910, upon receipt of patient data records from a device in the peripheral system 920, may store such patient data records in the data storage system 940. The peripheral system 920 does not need to be external to the device that includes the data processing system 910, user interface system 930, and data storage system 940.

The user interface system 930 may include a touch screen, touch pad, keypad, mouse, keyboard, another computer, or any device or combination of devices from which data is input to the data processing system 910. In this regard, and as noted above, although the peripheral system 920 is shown separately from the user interface system 930, the peripheral system 920 may be included as part of the user interface system 930. The user interface system 930 also may include a display device, a processor-accessible memory, or any device or combination of devices to which data is output by the data processing system 910. In this regard, if the user interface system 930 includes a processor-accessible memory, such memory may be part of the data storage system 940 even though the user interface system 930 and the data storage system 940 are shown separately in FIG. 9.

Figure 10:
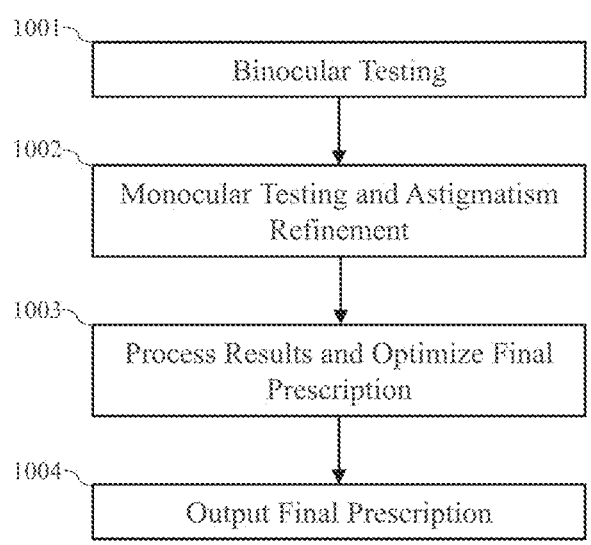
FIG. 10 is a flow chart showing steps in a method for determining a prescription for corrective lenses with a video screen.

FIG. 10 is a flow chart showing steps in a method for determining a prescription for corrective lenses according to an embodiment of the invention in which a user can receive an eye prescription at home or another location using a video screen utilizing the contrast sensitivity of the enhanced contrast font, in the same manner as a traditional autorefractor. Examples of items with a video screen that may be used include a laptop, desktop computer screen, cell phone, tablet, television, and projector.

Step 1001 of the method comprises binocular testing. The user is located a predetermined distance, such as 10 feet, away from the video screen. This distance can be measured in numerous ways, including using a physical tape measure, or using a laser, light, electromagnetic, or projection-based measuring device. Once the user is the predetermined distance away, the user will be shown a 10/100 letter on the video screen. The user then indicates whether they can see the letter clearly or not.

If the user indicates that she can see the 10/100 letter clearly, the 10/100 letter is gradually reduced in size (e.g., 10/100 to 10/90 to 10/80) until the user cannot see the letter clearly.

If the user indicates that she cannot see the 10/100 letter clearly, the user is instructed to walk forward until the user can see the letter clearly. The user is then instructed to input how much distance is now between the user and the video screen. This distance can be calculated in many ways, including those discussed above and including the input of how many heel-to-toe steps the user took toward the video screen.

The letter size and distance are recorded for the user's end state. This binocular testing of the user provides an indicator of the user's sight at a distance. It is noted that different values may be used for this step, and for subsequent steps. For example, the user could stand 20 feet away and the user could first be shown a 20/200 letter.

Next, step 1002 of the method comprises monocular testing and astigmatism refinement. For monocular testing, the letter size is reduced to the next visual acuity line from the letter size in step 1001 (e.g., the line immediately below in a Snellen chart). The user starts at 10 feet away, covers her left eye, and repeats the general process in step 1001. If the user indicates that she can see the letter clearly, the letter size is gradually reduced until the user cannot see the letter clearly. If the user indicates that she cannot see the letter clearly, the user is instructed to walk forward until the user can see the letter clearly; the user is then instructed to input how much distance is now between the user and the video screen. The letter size and distance are recorded for the user's end state. The user repeats the same process with her right eye covered.

For astigmatism refinement, a contrast wheel is shown on the screen. The user starts at 10 feet away, covers her left eye, and repeats the general process in step 1001. If the user indicates that she can see the contrast wheel clearly, the contrast wheel size is gradually reduced until the user cannot see the contrast wheel clearly. If the user indicates that she cannot see the contrast wheel clearly, the user is instructed to walk forward until the user can see the contrast wheel clearly; the user is then instructed to input how much distance is now between the user and the video screen. The contrast wheel size and distance are recorded for the user's end state. The user repeats the same process with her right eye covered.

In step 1003, the results are processed and the final prescription is optimized. Data for the five tests—binocular testing, monocular testing in both eyes, and astigmatism refinement in both eyes—are transmitted to a local or remote system for processing. Using this data and the methods and systems described herein, the user's eyeglass prescription is determined using predictive calculations and corrected-eyesight simulations. In step 1004, the patient's final prescription is output to the user.

The methods and systems described herein may be implemented using a computer program product. The computer program product can include one or more non-transitory, tangible, computer readable storage medium, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention.

Further, the methods and systems described herein may be implemented with the aid of: a brightness detector to measure the brightness of a room, which may help account for variances in pupil size; an eye movement detector to help provide full prescription notes for online users; and a physical distance measurement device to help determine the distance between the user or patient and the viewing screen in various embodiments.

The invention claimed is:

1. A method for determining a prescription for corrective lenses for a user, comprising:
positioning the user a first distance from a video screen;
displaying a first letter on the video screen;
instructing the user to indicate whether the first letter is clearly visible to the user;
receiving an indication from the user that the first letter is clearly visible to the user;
displaying a second letter on the video screen, wherein the second letter is a smaller size than the first letter;
receiving an indication from the user that the second letter is not clearly visible to the user;
instructing the user to cover one eye;
displaying a first contrast wheel on the video screen;
instructing the user to indicate whether the first contrast wheel is clearly visible to the user;
receiving an indication from the user that the first contrast wheel is clearly visible to the user;
displaying a second contrast wheel on the video screen, wherein the second contrast wheel is a smaller size than the first contrast wheel;
receiving an indication from the user that the second contrast wheel is not clearly visible to the user;
recording the size of the second letter, the size of the second contrast wheel, and the first distance from the video screen; and
using the size of the second letter, the size of the second contrast wheel, and the first distance from the video screen to determine the prescription for corrective lenses for the user.

2. The method of claim 1, further comprising:
positioning the user the first distance from a video screen;
displaying a third letter on the video screen;
instructing the user to indicate whether the third letter is clearly visible to the user;
receiving an indication from the user that the third letter is clearly visible to the user;
displaying a fourth letter on the video screen, wherein the fourth letter is a smaller size than the third letter;
receiving an indication from the user that the fourth letter is not clearly visible to the user;
recording the size of the fourth letter and first distance from the video screen; and
using the size of the fourth letter and first distance from the video screen to determine the prescription for corrective lenses for the user.

3. The method of claim 1, further comprising:
instructing the user to walk closer to the video screen to a second distance upon an indication from the user that the first letter is not clearly visible to the user.

4. The method of claim 3, further comprising:
recording the second distance from the video screen.

5. The method of claim 4, further comprising:
using the second distance from the video screen to determine the prescription for corrective lenses for the user.

6. The method of claim 1, further comprising:
instructing the user to walk closer to the video screen to a second distance upon an indication from the user that the first size of the contrast wheel is not clearly visible to the user.

7. The method of claim 6, further comprising:
recording the second distance from the video screen.

8. The method of claim 7, further comprising:
using the second distance from the video screen to determine the prescription for corrective lenses for the user.

* * * * *